US008748851B2

(12) United States Patent
Li et al.

(10) Patent No.: US 8,748,851 B2
(45) Date of Patent: Jun. 10, 2014

(54) MATERIAL AGING APPARATUS

(71) Applicant: Industrial Technology Research Institute, Hsinchu (TW)

(72) Inventors: Yu-Tai Li, Taichung (TW); Yu-Hsien Lee, Chiayi (TW); Hsien-Chen Ma, Hsinchu County (TW); Chen-Wei Chen, Changhua County (TW); Hung-Sen Wu, Taoyuan County (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 13/674,067

(22) Filed: Nov. 11, 2012

(65) Prior Publication Data

US 2014/0084180 A1    Mar. 27, 2014

(30) Foreign Application Priority Data

Sep. 21, 2012    (TW) .............................. 101134832 A

(51) Int. Cl.
*G21K 5/00*    (2006.01)

(52) U.S. Cl.
USPC ........... 250/492.1; 356/32; 356/35.5; 356/51; 356/73; 73/170.27; 73/514.19

(58) Field of Classification Search
USPC ........ 250/492.1, 504 R; 356/32, 35.5, 51, 73; 73/170.27, 514.19, 61.4
See application file for complete search history.

(56) References Cited

U.S. PATENT DOCUMENTS

| 4,122,383 | A | 10/1978 | Frosch et al. |
| 4,747,645 | A | 5/1988 | Rudzki |
| 6,525,493 | B2 | 2/2003 | Grossman et al. |
| 6,820,509 | B2 | 11/2004 | Lewandowski et al. |
| 7,696,461 | B2 | 4/2010 | Sinton et al. |
| 2003/0200824 | A1* | 10/2003 | Lewandowski et al. ..... 73/865.6 |
| 2012/0234807 | A1* | 9/2012 | Sercel et al. ............. 219/121.69 |

FOREIGN PATENT DOCUMENTS

CN        1841046        10/2006

OTHER PUBLICATIONS

Radue et al., "A comparison of degradation in three amorphous silicon PV module technologies," Solar Energy Materials & Solar Cells 94 (3), Mar. 2010, pp. 617-622.
Rossi et al., "Accelerated stability test for amorphous silicon solar cells," Appl. Phys. Lett. 60 (14), Apr. 6, 1992, pp. 1709-1711.
Stutzmann et al., "Pulsed-light soaking of hydrogenated amorphous silicon," Physical Review B 50 (16), Oct. 15, 1994, pp. 11592-11605.
Spanakis et al., "Metastable photoexpansion of hydrogenated amorphous silicon produced by exposure to short laser pulses," Journal of Non-Crystalline Solids 352 (5), May 2006, pp. 429-433.
Kurova et al., Abstract of "The Effect of Illumination on Dark Conductivity and Photoconductivity of Hydrogenated Amorphous Silicon Layered Films," Moscow University Physics Bulletin 64 (5), Oct. 2009, p. 1.
Fujikake et al., "Light-induced recovery of a-Si solar cells," Solar Energy Materials and Solar Cells 34, Sep. 1994, pp. 449-454.

* cited by examiner

*Primary Examiner* — Nicole Ippolito
(74) *Attorney, Agent, or Firm* — Jianq Chyun IP Office

(57) ABSTRACT

An aging apparatus including a pulse laser, a beam expansion assembly, and a platform configured to carry an object is provided. The pulse laser transmits a first beam to the beam expansion assembly. The beam expansion assembly expands the first beam to a second beam and projects the second beam onto the object.

12 Claims, 5 Drawing Sheets

MATERIAL AGING APPARATUS

CROSS-REFERENCE TO RELATED APPLICATION

This application claims the priority benefit of Taiwan application serial no. 101134832, filed on Sep. 21, 2012. The entirety of the above-mentioned patent application is hereby incorporated by reference herein and made a part of this specification.

TECHNICAL FIELD

The technical field relates to a material aging apparatus, and more particularly to, a light aging equipment.

BACKGROUND

Solar energy is an inexhaustible and non-polluting energy, and has been a focus of most attentions in terms of solving current problems of pollution and shortage faced by fossil energy. Wherein, a solar cell with its ability of directly converting the solar energy into electricity has become one of the most important options of alternative energies.

Generally, such product is used in an outdoor environment for a long time, and a tolerability thereof is often greatly influenced by the environment and climate. For instance, both the solar cell itself or a packaging material thereof, under a condition of operating under the sun light for a long time, a material degradation thereof causing by ultraviolet (UV) light is most likely to happen. Therefore, in order to enhance a service life of the product, and to obtain tolerability parameters of the product within a short amount of time, an accelerated aging test is often performed on the product.

The conventional light aging equipments mostly use solar simulator light sources, xenon lamps or UV lamps as light sources for the accelerated aging test, but there are still the following problems in need to be solved; limited by operation modes of the conventional light sources, the product is mostly irradiated by a large area light source, and thus an illuminance on the product in a unit area is also weakened; and herein, in order to enhance a rate of aging, a means to enhance an intensity of the light source is often used, but this may easily result in a temperature increase of the product; namely, the conventional light sources may easily cause the product to be heated, and thereby influencing aging factors of the product. Furthermore, the abovementioned aging light sources are mostly adopted with large scale area aging, and thus partial irradiations on the products and projections of different illuminance light sources on partial regions are not easily. Moreover, the abovementioned light sources all perform aging irradiations on the product with a certain range of wavelengths, and are not able to provide a single wavelength light source or to fine-tune a wavelength range thereof according to the conditions.

According to the foregoing, performing a light aging test on a product with precise conditions is still a subject in need of further study.

SUMMARY

One of exemplary embodiments provides a material aging apparatus using a pulse laser to enhance a light aging efficiency in an object.

One of exemplary embodiments provides a material aging apparatus including a pulse laser, a beam expansion assembly and a platform. The platform is configured to carry an object. The pulse laser transmits a first beam to the beam expansion assembly. The beam expansion assembly expands the first beam to a second beam and projects the second beam onto the object.

Several exemplary embodiments accompanied with figures are described in detail below to further describe the disclosure in details.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

DETAILED DESCRIPTION OF DISCLOSED EMBODIMENTS

Figure 1:
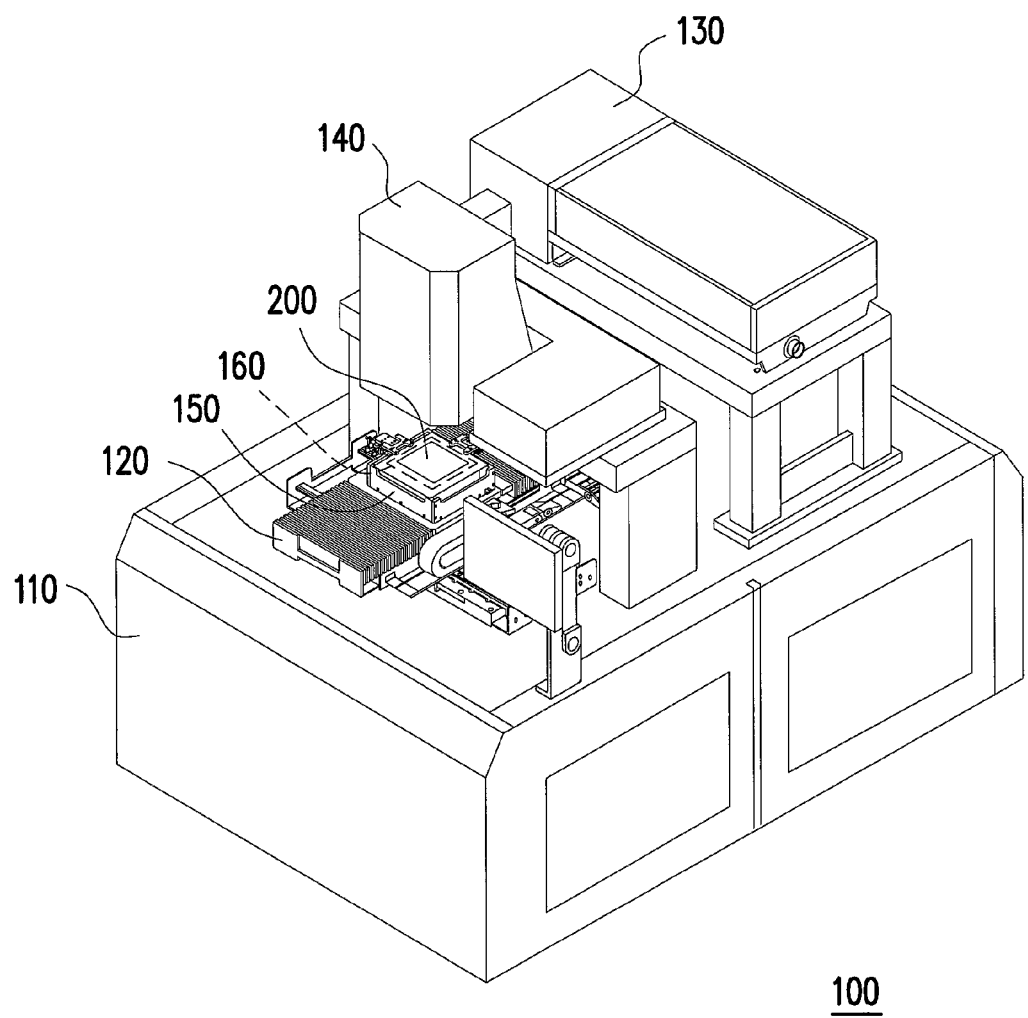
FIG. 1 is a schematic diagram illustrating a material aging apparatus according to an embodiment.
Figure 2:
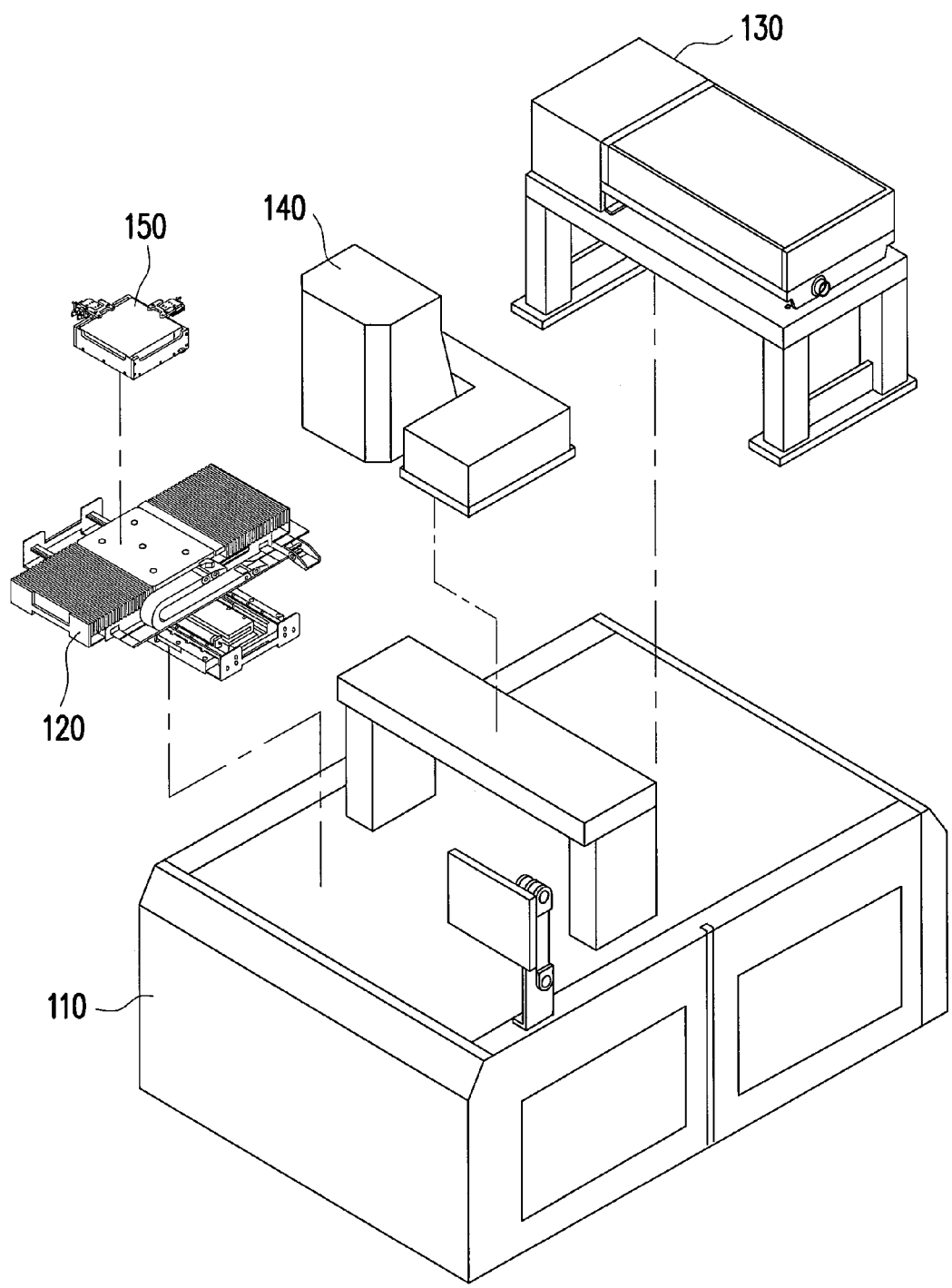
FIG. 2 is an exploded view illustrating the 1 material aging apparatus of FIG. 1.

FIG. 1 is a schematic diagram illustrating a material aging apparatus according to an embodiment. FIG. 2 is an exploded view illustrating the material aging apparatus of FIG. 1. Referring to FIG. 1 and FIG. 2 at the same time, in the present embodiment, the material aging apparatus 100 is configured to perform a light aging test to an object 200 so as to acquire a material weatherability. The material aging apparatus 100 includes a base 110, a platform 120, a pulse laser 130 and a beam expansion assembly 140. The base 110 is, for example, a granite base, and the platform 120, the pulse laser 130 and the beam expansion assembly 140 are mounted thereon. The platform 120 is, for example, an X axis-Y axis moving platform configured to carry and drive the object 200 to move. The beam expansion assembly 140 is located above the platform 120 and the object 200. A beam emitted by the pulse laser 130 is projected onto the object 200 on the platform 120 through the beam expansion assembly 140. In addition, the material aging apparatus 100 further includes a carrier 150 and a temperature control module 160 disposed on the platform 120, wherein the carrier 150, for example, fixes the object 200 thereon by a means of vacuum suction, and the temperature control module 160 is disposed within the carrier 150 and has a water cooling circuit (not shown) configured to provide a cooling effect to the object 200 on the carrier 150.

Figure 3:
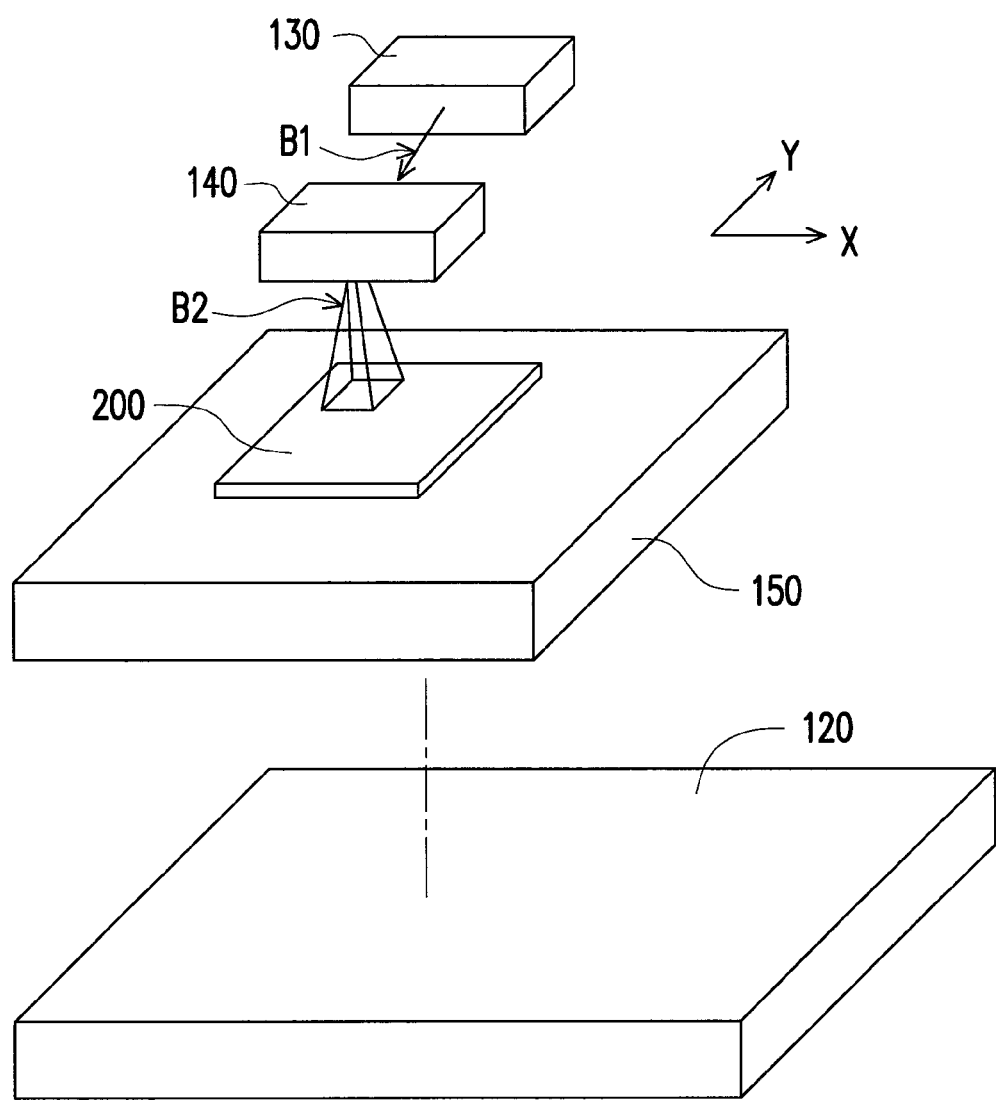
FIG. 3 is a simplified schematic diagram illustrating the material aging apparatus 100 of FIG. 1.

FIG. 3 is a simplified schematic diagram illustrating the material aging apparatus 100 of FIG. 1. Referring to FIG. 3, the pulse laser 130 is configured to transmit the first beam B1 to the beam expansion assembly 140, and the beam expansion assembly 140 expands the first beam B1 to a second beam B2 and projects the second beam B2 onto a surface of the object 200. Herein, the first beam B1 and the second beam B2 with a wavelength range between 280 nm to 400 nm are projected from the pulse laser 130 of the present embodiment, which is namely a UV light having a significant influence on a material degradation, as an irradiation light source for the light aging.

In the present embodiment, the pulse laser 130 is a short-pulse laser, wherein pulse duration thereof is less than 1 μs, and pulse repetition rate thereof is greater than or equal to 10 Hz, so that the pulse laser 130 is characterized as projecting beam with periodic and instantaneous high energy, and the object 200 illuminated by the beam of the pulse laser 130 with periodic and instantaneous highly intensified but low accumulated energy aging effect.

For instance, when the object 200 is a solar cell module, taking the pulse laser 130 with energy of 100 mJ, pulse duration of 5 ns and pulse repetition rate of 10 Hz as an example, average power density of the second beam B2, which is projected on the object 200 through the beam expansion assembly 140, can be adjusted between 10 kw/m² to 0.1 kw/m² according to different beam expansion areas; however, due to characteristics of the pulse laser 130, instant irruption subjected to the object 200 (converted with 5 ns) is up to 20 Mkw/m² to 0.2 Mkw/m², and under the effect of this moderate average power density, the light aging effecting on the solar cell module may be accelerated without burning and melting the module or causing a recrystallization (tempering). Similarly, when the object 200 is a polymer material, the average power density of the second beam B2 is between 5 kw/m² to 0.1 kw/m² and the light aging effecting on the object 200 may be accelerated without damaging the polymer material.

In addition to providing instantaneous high power density aging characteristics, the pulse laser 130, with its characteristics, is different from the conventional persistent irradiation light source, and thus energy irradiated on the object 200 is not being accumulated; namely, the temperature of the object 200 is not going to be gradually increased due to persistent irradiation, and therefore capable of effectively reducing influences on the light aging test of the object 200 due to thermal effect. In other word, the material aging apparatus 100 of the present embodiment may control the temperature of object 200 merely via the temperature control module 160 disposed within the carrier 150. In the present embodiment, the temperature control module 160 may maintain the temperature of the object 200 on the carrier 150 between 10° C. to 60° C., such that, in addition to avoiding heat accumulation to affect the light aging, it is also capable of effectively avoiding the material from having a recrystallization (annealing) phenomenon and even a damage due to burning and melting.

Figure 4:
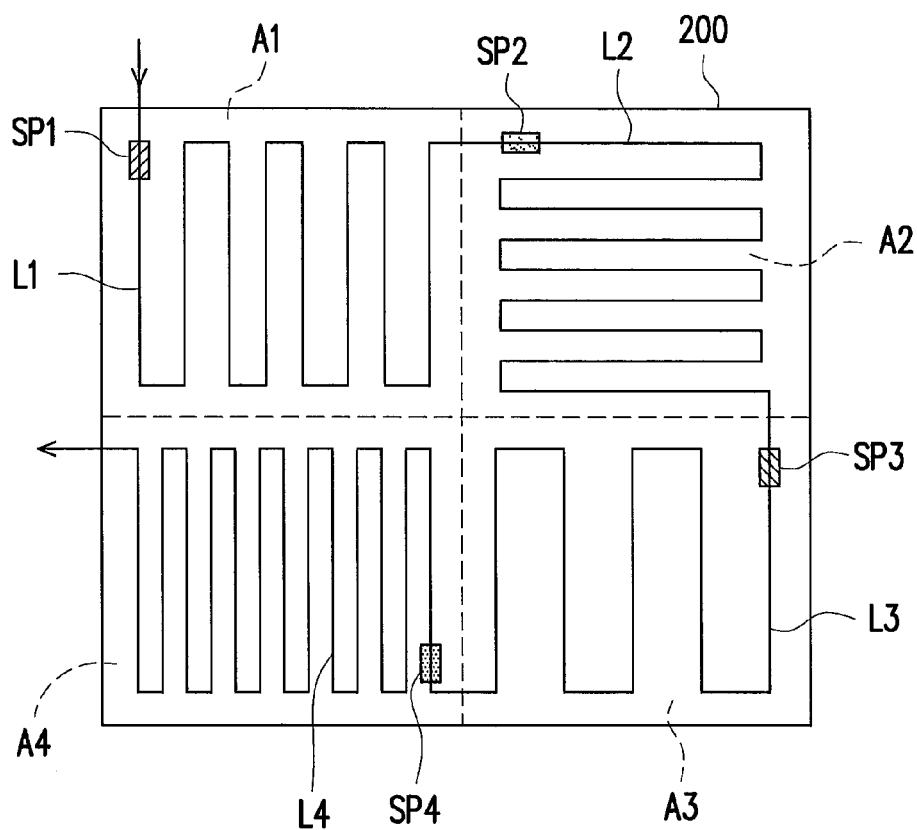
FIG. 4 is a schematic diagram illustrating a moving path of a second beam of FIG. 3 for forming spots on an object.

FIG. 4 is a schematic diagram illustrating a moving path of a second beam of FIG. 3 for forming spot on an object. Referring to FIG. 3 and FIG. 4 at the same time, in the present embodiment, by using the platform 120 to actuate the object 200 to move, users are enable to control the moving path of the second beam B2 on the object 200, and further adjust the moving path, power and wavelength range of the second beam B2 according to testing requirements.

For instance, the surface of the object 200 is separated into four areas A1 to A4, and enables the second beam B2 to respectively pass through the surface of the object 200 with different paths in areas A1 to A4, so that the power, wavelength and even irradiation area of the second beam B2 are also changed along the paths at the same time. As a result, in the area A1, a spot SP1 formed by the second beam B2 on the object 200 is scanned via a path L1. Similarly, in the areas A2 to A4, spots SP2 to SP4 are also capable of being respectively scanned via paths L2 to L4, wherein the paths L1 to L4 respectively have different density degrees. As a result, the users can perform irradiations on the same object 200 via the spots formed with multiple requirements, and therefore a tolerability parameter of the object 200 against the light aging may be obtained in a more efficient way. Moreover, via the pulse laser 130 with adjustable wavelength, it is also able to produce selective ageing effects to the object 200 by targeting some specific wavelengths, and the users are therefore able to figure out a relative relationship of the material characteristics of the object 200 in correspondence to specific absorption wavelengths.

Figure 5:
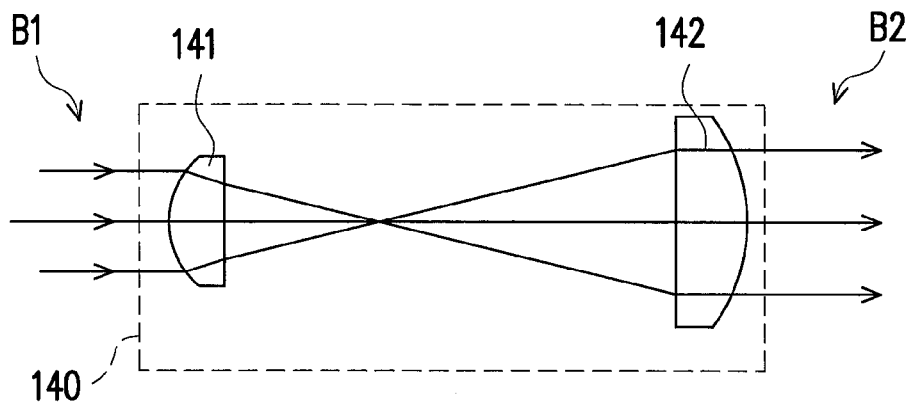
FIG. 5 is a schematic diagram illustrating the beam expansion assembly of FIG. 1.

Moreover, in order to successfully achieve the above mentioned effects, the first beam B1 projected from the pulse laser 130 has to be firstly expanded by the beam expansion assembly 140 and then projected onto the object 200 as the second beam B2 to form the required spots. FIG. 5 is a schematic diagram illustrating the beam expansion assembly of FIG. 1. Referring to FIG. 5, the beam expansion assembly 140 is composed of a plurality of optical elements (lens group) 141, 142, so as to expand a spot area of the first beam B1 and shape the spot area to a desired contour; namely, in the present embodiment, the speck area of the second beam B2 is larger than a spot area of the first beam B1 的 spot area. As illustrated in FIG. 4, the spots SP1 to SP4 with areas larger than 1 cm² are formed on the object 200 of 20 cm², and then the object 200 is scanned by the spots SP1 to SP4 via the different paths illustrated in FIG. 4 in order to accelerate the light aging effect on the object 200. In addition, the energy per unit area of the second beam B2, after the beam expansion, is smaller than the energy per unit area of the first beam B1, and therefore the energy subjected to the object 200 is also reduced at the same time in order to prevent the temperature from being too high.

Figure 6:
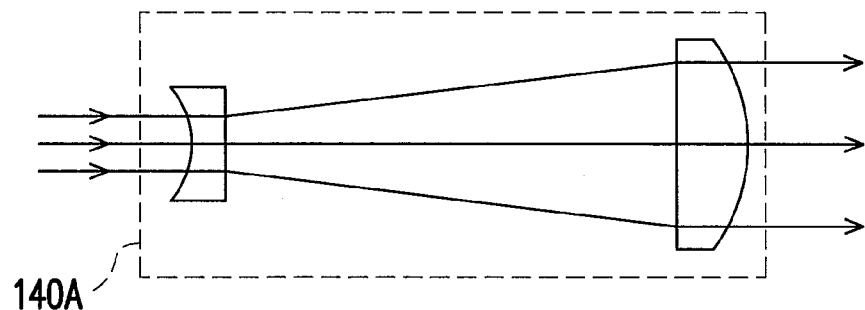
FIG. 6 is a schematic diagram illustrating a beam expansion assembly according to another embodiment.
Figure 7:
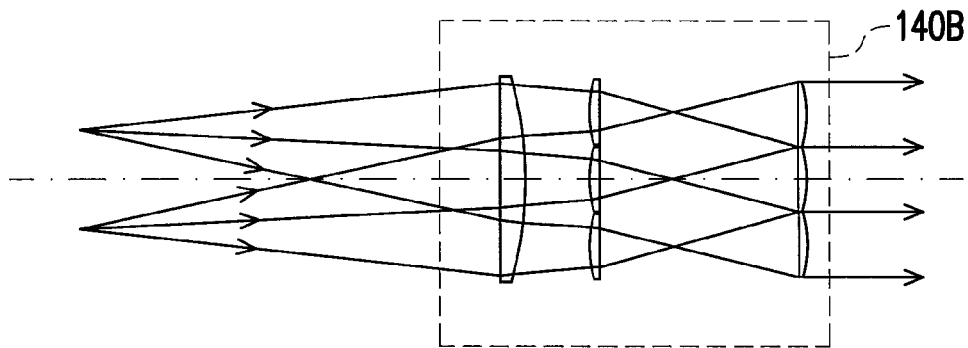
FIG. 7 is a schematic diagram illustrating a beam expansion assembly according to still another embodiment.

Compositions of the beam expansion assembly are not limited herein, any element capable of beam expanding and shaping to the first beam B1 emitted by the pulse laser 130 may be adapted to the present embodiment. FIG. 6 is a schematic diagram illustrating a beam expansion assembly according to another embodiment, wherein the beam expansion assembly 140A of the present embodiment is a Galilean beam expander, which in terms of the structure is different form a Keplerian beam expander illustrated in FIG. 5 but can achieve an effect similar to beam expansion. In addition, FIG. 7 is a schematic diagram illustrating a beam expansion assembly according to still another embodiment, wherein the beam expansion assembly 140B, targeting the two beams respectively, can perform the beam expansion and shaping effects at the same time. Accordingly, the users, targeting the area size and appearance of the object, can further configure the contours and sizes of the required spots via the beam expansion assemblies.

In summary, in the embodiments of the disclosure, the material aging apparatus reduces the average illumination per unit area thereof via using the short pulse laser as the light source and adjusting the beam area thereof through the beam expansion assembly, and therefore is capable of using the light source with a lower accumulated energy yet a most intensified instant energy to irradiate the object, thereby effectively improving problems caused by the conventional light-tube type or light-box type light aging equipments. Furthermore, since the pulse laser can provide the light aging irradiation to partial areas of the object, and in coordination with the movable platform, the pulse laser irradiates the object via different powers, different paths and different wavelengths, and completes light aging irradiations of different requirements on the same object. As such, the material aging apparatus is able to figure out the light aging parameters of the object in a more efficient way.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A material aging apparatus comprising:
   a pulse laser;
   a beam expansion assembly; and
   a platform configured to carry an object, the pulse laser providing a first beam transmitted to the beam expansion assembly, and wherein the beam expansion assembly expands the first beam to a second beam and projects the second beam onto the object, and the object is light-aged by the second beam without melting, burning, or damaging.

2. The material aging apparatus as recited in claim 1, wherein the platform is a moving platform, and the object moves along the moving platform so that the second beam is projected onto the object via at least one path.

3. The material aging apparatus as recited in claim 2, wherein the object is separated into a plurality of aging areas, the second beam is projected onto the aging areas via a plurality of paths, and different aging areas comprise different paths with different density.

4. The material aging apparatus as recited in claim 1, wherein power of the second beam is adjustable.

5. The material aging apparatus as recited in claim 1, wherein wavelength of the second beam is adjustable.

6. The material aging apparatus as recited in claim 1, wherein an adjustable range of the wavelength of the first beam is between 280 nm to 400 nm.

7. The material aging apparatus as recited in claim 1, wherein the object is a solar cell, and the average power density of the second beam is between 10 kw/m$^2$ to 0.1 kw/m$^2$.

8. The material aging apparatus as recited in claim 1, wherein the object is a polymer material, and the average power density of the second beam is between 5 kw/m$^2$ to 0.1 kw/m$^2$.

9. The material aging apparatus as recited in claim 1, wherein the pulse duration of the pulse laser is less than 1 μs, and the pulse repetition rate of the pulse laser is greater than or equal to 10 Hz.

10. The material aging apparatus as recited in claim 1, wherein an area of the second beam projected onto the object is larger than 1 cm$^2$.

11. The material aging apparatus as recited in claim 1 further comprising:
    a temperature control module connected to the platform, so as to adjust temperature of the platform at a place carrying the object.

12. The material aging apparatus as recited in claim 11, wherein an adjustable range of the temperature of the platform is between 10° C. to 60° C.

* * * * *